(12) United States Patent
Coughlin

(10) Patent No.: US 8,563,019 B2
(45) Date of Patent: Oct. 22, 2013

(54) NON-AQUEOUS GENERATION OF CHLORINE DIOXIDE

(75) Inventor: Michael F. Coughlin, Cincinnati, OH (US)

(73) Assignee: Diversey, Inc., Sturtevant, WI (US)

( * ) Notice: Subject to any disclaimer, the term of this patent is extended or adjusted under 35 U.S.C. 154(b) by 76 days.

(21) Appl. No.: 12/933,295

(22) PCT Filed: Mar. 19, 2009

(86) PCT No.: PCT/US2009/037672
§ 371 (c)(1),
(2), (4) Date: Sep. 17, 2010

(87) PCT Pub. No.: WO2009/117581
PCT Pub. Date: Sep. 24, 2009

(65) Prior Publication Data
US 2011/0020472 A1    Jan. 27, 2011

Related U.S. Application Data

(60) Provisional application No. 61/038,269, filed on Mar. 20, 2008.

(51) Int. Cl.
| | | |
|---|---|---|
| *A01N 25/00* | (2006.01) | |
| *A61K 33/20* | (2006.01) | |
| *A61K 31/19* | (2006.01) | |
| *A61K 31/20* | (2006.01) | |

(52) U.S. Cl.
USPC ............ 424/405; 424/665; 514/557; 514/558

(58) Field of Classification Search
USPC .......................... 424/405, 665; 514/557, 558
See application file for complete search history.

(56) References Cited

U.S. PATENT DOCUMENTS

| | | | | |
|---|---|---|---|---|
| 5,364,650 | A | * | 11/1994 | Guthery ........................ 510/111 |
| 5,405,549 | A | * | 4/1995 | Pitochelli ................. 252/187.21 |
| 5,693,252 | A | | 12/1997 | Pitochelli |
| 5,707,546 | A | * | 1/1998 | Pitochelli ................. 252/187.21 |
| 6,524,624 | B1 | | 2/2003 | Morelli et al. |
| 6,663,902 | B1 | | 12/2003 | Hei et al. |
| 6,761,872 | B2 | | 7/2004 | Roensch et al. |
| 2004/0022676 | A1 | | 2/2004 | Hamilton et al. |
| 2008/0057555 | A1 | | 3/2008 | Nguyen |

OTHER PUBLICATIONS

"The Existence of a Uronic Acid Ester in Young Wood of *Eucalyptus regnans*", D H Foster et al., Australian Journal of Scientific Research, vol. 3, No. 3, Jan. 1, 1950, pp. 504-511.

"Chlorine Oxygen Acids and Salts, Chlorous Acid, Chlorites, and Chlorine Dioxide" J J Kaczur et al., Kirk-Othmer Encyclopedia of chemical Technology, Dec. 4, 2000, pp. 1-26.
The International Search Report prepared by the Korean Intellectual Property Office for PCT/US2009/037672.
Deshwal, Bal Raj, "Manufacture of Chlorine Dioxide from Sodium Chlorite: Process Chemistry". J. Ind. Eng. Chem., vol. 11, No. 1, pp. 125-136 (2005).
Gunstone, F.D., "Fatty Acids" In: "Comprehensive Organic Chemistry, vol. 5", Jan. 1, 1979, Pergamon Press, Oxford, U.K., XP55017975, ISBN: 0-08-0213171-0, pp. 587-595.
Orchin, M., et al., "Fatty Acids, Saturated Fatty Acids, Unsaturated Fatty Acids" In: "The Vocabulary of Organic Chemistry", Jan. 1, 1980, John Wiley & Sons, New York, U.S.A., XP55017977, ISBN: 978-0-47-104491-8,pp. 466-467.
Wolfe, D.H., "19.2 Fatty Acids" In: "Essentials of General, Organic and Biological Chemistry", Jan. 1, 1986, McGraw-Hill Book Company, New York, U.S.A., XP55017980, ISBN: 978-0-07-071415-1 pp. 377-380.
Falbe, J., et al., "Fettsauren" In: "Rompp Chemie Lexikon, 9. Auflage", Jan. 1, 1990, Georg Thieme Verlag, Stuttgart, XP55017981, ISBN: 978-3-13-734709-5, pp. 1343-1345.
Jordan, S., et al., "3 Lipids" In: "Food Chemistry", Jan. 1, 1999, Springer Verlag, Berlin, Germany, XP55017988, ISBN: 978-3-54-064704-1, pp. 152-158.
European Patent Office Action for Application No. 09722983.5 dated Jul. 31, 2012 (7 pages).
Search Report from the European Patent Office for Application No. 09722983.5 dated Mar. 1, 2012 (6 pages).
Wise, L.E., Murphy, M. and D'Addieco, A.A., Paper Tr. J., 122 (2): 35-43 (1946) (12 pgs).
Office Action from the European Patent Office for Application No. 09722983.5 dated Mar. 1, 2013 (7 pages).
Erich Schmidt et al: "Zur Kenntnis der naturlichen EiweiBstoffe, I. Mitteilung: Verhalten von Chlordioxyd gegenuber organischen Verbindungen", Ber. dtsch. Chem. Ges. A/B, Jun. 17, 1922, pp. 1529-1534, XP55053703, DOI: 10.1002/cber.19220550606 (14 pages).

* cited by examiner

*Primary Examiner* — Sue Liu
*Assistant Examiner* — Nathan W Schlientz
(74) *Attorney, Agent, or Firm* — Michael Best & Friedrich LLP

(57) ABSTRACT

Disclosed is a method of making a non-aqueous chlorine dioxide solution by combining a chlorite salt and a non-aqueous carboxylic acid and the non-aqueous chlorine dioxide solution made by this method. Also disclosed are methods of disinfecting an object by applying the non-aqueous chlorine dioxide solution to the object and methods of disinfecting a liquid by adding the non-aqueous chlorine dioxide solution to the liquid.

9 Claims, No Drawings

NON-AQUEOUS GENERATION OF CHLORINE DIOXIDE

BACKGROUND

Chlorine dioxide is commonly used as a disinfectant and sterilizing agent in diverse applications ranging from bleaching wood pulp to treatment of drinking water or wastewater. Traditional methods for generating aqueous solutions containing chlorine dioxide include reacting an acid with sodium chlorite in an aqueous solution to produce chlorous acid and subsequently oxidizing the chlorous acid to chlorine dioxide via catalysis or chlorination. In an aqueous solution, chlorine dioxide is relatively unstable. Therefore, aqueous solutions of chlorine dioxide are traditionally produced at the application site and must be used within a short period of time.

SUMMARY

In one aspect, methods of making a non-aqueous chlorine dioxide solution are disclosed. The non-aqueous chlorine dioxide solution is made by combining a chlorite salt with a non-aqueous carboxylic acid. The non-aqueous chlorine dioxide solution made by the method is also disclosed.

In another aspect, methods of disinfecting an object are provided. The methods include applying the non-aqueous chlorine dioxide solution to the object.

In yet another aspect, methods of disinfecting a liquid are provided. The methods include adding the non-aqueous chlorine dioxide solution to the liquid.

In a still further aspect, a non-aqueous chlorine dioxide solution is provided. The solution comprises chlorine dioxide and a non-aqueous carboxylic acid.

Other aspects of the invention will become apparent by consideration of the detailed description. Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited.

DETAILED DESCRIPTION

Disclosed herein are methods for the non-aqueous generation of chlorine dioxide and methods of using non-aqueous chlorine dioxide. In particular, non-aqueous chlorine dioxide is produced by combining a chlorite salt with a non-aqueous carboxylic acid to produce a non-aqueous solution of chlorine dioxide. The resultant non-aqueous solution of chlorine dioxide may be used as a disinfectant or sanitizing agent to treat objects or may be added to liquids.

Method of Making the Non-Aqueous Chlorine Dioxide Solution

Non-aqueous chlorine dioxide may be made by combining a chlorite salt with a non-aqueous carboxylic acid. The chlorite salt is suitably added to the non-aqueous carboxylic acid. Once the chlorite salt is added, the solution may be mixed or agitated by any means known to those of skill in the art. The chlorite salts generally have the formula $M^{+n}(ClO_2)^n$, wherein n is a positive integer. The non-aqueous carboxylic acids generally have the formula RCOOH, wherein R is an aliphatic group. The following reaction scheme generally represents the reaction occurring upon mixing a chlorite salt with a non-aqueous carboxylic acid:

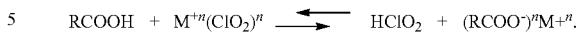

$$RCOOH + M^{+n}(ClO_2)^n \rightleftharpoons HClO_2 + (RCOO^-)^n M^{+n}.$$

Thus, the combination results in generation of chlorine dioxide having the characteristic yellow color of chlorine dioxide. In the Examples below, sodium chlorite was combined with octanoic acid to produce a non-aqueous solution of chlorine dioxide as evidenced by the appearance of the characteristic yellow color. The combination results in at least about 30%, 40%, 50%, 60%, 70% of the theoretical yield of chlorine dioxide.

Those of skill in the art will appreciate that the chlorite salt may be added to the non-aqueous carboxylic acid at a variety of concentrations. Solution having relatively high initial concentrations of chlorite salt will yield more concentrated chlorine dioxide solutions. For example, at least about 0.1 g of chlorite salt may be added per liter of non-aqueous carboxylic acid. Suitably at least 0.005 g of chlorite salt is added per liter of non-aqueous carboxylic acid, more suitably at least about 0.05 g chlorite salt is added per liter of acid, more suitably 0.5 g, 1.0 g, 2.0 g or even 5.0 g of chlorite salt are added per liter of non-aqueous carboxylic acid.

Chlorite salts known to those skilled in the art may be used to generate the chlorine dioxide. Exemplary chlorite salts include, but are not limited to, alkali metal chlorites, alkaline earth metal chlorites, transition metal chlorites, inner transition metal chlorites and polymeric chlorite salts. In particular, the chlorite salt may comprise sodium chlorite $NaClO_2$, potassium chlorite $KClO_2$, lithium chlorite $LiClO_2$, calcium chlorite $Ca(ClO_2)_2$, barium chlorite $Ba(ClO_2)_2$, magnesium chlorite $Mg(ClO_2)_2$ or combinations thereof. Combinations of two or more chlorite salts may also be used. The chlorite salt is added in solid form and, depending upon the grade, may contain inactive salt impurities. The chlorite salt may be in any form, such as particles, granules or powdered.

The aliphatic group of the non-aqueous carboxylic acids suitable for use in the invention may have a carbon chain length up to 18 and may be branched or unbranched and substituted or unsubstituted. Exemplary saturated non-aqueous carboxylic acids include, but are not limited to, acetic acid, lactic acid, valeric acid (pentanoic acid, $C_5$), caproic acid (hexanoic acid, $C_6$), enanthic acid (heptanoic acid, $C_7$), caprylic acid (octanoic acid, $C_8$), pelargonic acid (nonanoic acid, $C_9$), capric acid (decanoic acid, $C_{10}$), undecyclic acid (undecanoic acid, $C_{11}$), lauric acid (dodecanoic acid, $C_{12}$), isobutyric acid (2-methyl propanoic acid), isovaleric acid (3-methyl butanoic acid), pivalic acid (2,2-dimethyl propanoic acid). An exemplary substituted non-aqueous carboxylic acid includes, but is not limited to, ricinoleic acid (hydroxy-substituted $C_{18}$). Notably, combinations of non-aqueous carboxylic acids may also be used. Other suitable non-aqueous carboxylic acids are known to those of skill in the art.

The choice of non-aqueous carboxylic acid may be based upon a number of factors including, but not limited to, the ease of handling, corrosivity, reaction rate and cost. Suitably the non-aqueous carboxylic acid is in liquid form at 50° C. or below. In particular, suitable non-aqueous carboxylic acids are water-insoluble liquids.

Other components may optionally be added to the non-aqueous chlorine dioxide solution to impart various additional properties to the solution. Such ingredients may include, but are not limited to, hydrotropes, dispersants, wetting agents, additional antimicrobials, and combinations thereof. These additives may be added before, during and/or after combining the chlorite salt with the non-aqueous carboxylic acid.

Hydrotropes may be added to enhance the wetting nature of the non-aqueous chlorine dioxide solution and/or enhance compatibility of the non-aqueous chlorine dioxide solution with aqueous environments. Exemplary hydrotropes include, but are not limited to, toluene sulfonate, xylene sulfonate, cumene sulfonate and mixtures thereof. A hydrotrope may be added to the non-aqueous carboxylic acid before, during and/or after mixing with the chlorite salt. Suitably the hydrotrope is added in an amount effective to enhance penetration of chlorine dioxide into an object being disinfected or to enhance miscibility with an aqueous liquid. Combinations of hydrotropes may be used as well.

Suitable dispersants may include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, phosphonoamides, thiophosphonamides and phosphoramides; thiazoles (e.g., 2,5-dimercapto-1,3,4-thiadiazoles, mercaptobenzothiazoles and derivatives thereof); triazoles (e.g., alkyltriazoles and benzotriazoles); and copolymers which contain a carboxylate ester with one or more additional polar functional groups, including amine, amide, imine, imide, hydroxyl and carboxyl (e.g., products prepared by copolymerization of long chain alkyl acrylates or methacrylates with monomers of the above function). Derivatives of these dispersants, e.g., borated dispersants such as borated succinimides, may also be used. As will be appreciated by those of skill in the art, dispersants may be added in an amount effective to enhance the miscibility of the non-aqueous chlorine dioxide solution with an aqueous solution or an aqueous environment. Combinations of dispersants may be used.

Typical wetting agents may include, but are not limited to, alcohols (e.g., methanol, ethanol, propanol and butanol), glycols (e.g., ethylene glycol), polyethylene glycols, ketones (e.g., methyl ethyl ketone), sodium lauryl sulfate, polyoxyethylene sorbitan fatty acid esters, polyoxyethylene alkyl ethers, sorbitan fatty acid esters, polyoxyethylene castor oil derivatives, docusate sodium, quaternary ammonium compounds, sugar esters of fatty acids and glycerides of fatty acids. As will be appreciated by those of skill in the art, wetting agents may be added in an amount effective to lower the surface tension of the non-aqueous chlorine dioxide solution and allow for enhanced coating and penetration of objects. Combinations of wetting agents may be used.

Antimicrobial agents may include, but are not limited to, disinfectants, antiseptics and preservatives. Antimicrobial agents may include, but are not limited to, phenols, such as iodophores, halo- and nitrophenols and substituted bisphenols such as 4-hexylresorcinol, 2-benzyl-4-chlorophenol and 2,4,4'-trichloro-2'-hydroxydiphenyl ether; organic and inorganic acids and their esters and salts, such as dehydroacetic acid, peroxycarboxylic acids, peroxyacetic acid, methyl p-hydroxy benzoic acid; cationic agents, such as quaternary ammonium; aldehydes, such as glutaraldehyde; antimicrobial dyes, such as acridines, triphenylmethane dyes and quinones; and halogens, such as iodine and chlorine compounds. The antimicrobial agents can be used in an amount sufficient to provide the desired antimicrobial properties. Those of skill in the art will appreciate that combinations of antimicrobial agents could be added to the non-aqueous chlorine dioxide solution. In some embodiments, the antimicrobial agents may act synergistically with the chlorine dioxide in the non-aqueous chlorine dioxide solution to produce enhanced antimicrobial properties.

Method of Making the Non-Aqueous Chlorine Dioxide Solutions

In practice, solid chlorite salt and liquid non-aqueous carboxylic acids are combined to produce a non-aqueous chlorine dioxide solution. The solution may be optionally mixed by any method known to those of skill in the art, such as shaking or stirring. The solution changes over time from colorless to yellow as chlorine dioxide is generated. The concentration of chlorine dioxide in the resultant solution will depend upon the amount of chlorite salt added to the non-aqueous carboxylic acid. In some embodiments, the amount of chlorite salt added is at or above the saturation point of the solution comprising the non-aqueous carboxylic acid. Optional components, such as those mentioned above, may be added before, during and/or after the production of chlorine dioxide. The non-aqueous chlorine dioxide solutions can be stored in a closed container in a light-free environment to minimize decomposition. Alternatively, the non-aqueous chlorine dioxide solution can be stored in a container that blocks or reduces the amount of light, such as a dark colored container.

In one embodiment, sodium chlorite and octanoic acid are combined to produce the non-aqueous chlorine dioxide solution. A hydrotrope, such as cumene sulfonate, may be added to improve the wetting nature of the solution, such that the non-aqueous chlorine dioxide solution can be used in an aqueous environment and to allow for better penetration into recesses, pores or crevices of an object to which it is applied.

Non-aqueous solutions of chlorine dioxide are more stable than aqueous solutions of chlorine dioxide. In the Examples below, chlorine dioxide in octanoic acid retained its yellow color for more than one year when stored in a closed container and protected from light. The non-aqueous chlorine dioxide solutions may be stable for at least about one month, particularly at least about three months, and more particularly for at least about nine months or even more than one year or longer when stored at room temperature in the absence of light. It is envisioned that when using non-aqueous carboxylic acids having a vapor pressure that is less than that of water, loss of chlorine dioxide due to vaporization will be less than that found with aqueous chlorine dioxide solutions. For example, the vaporization of chlorine dioxide from octanoic acid is likely less than that from aqueous solutions because the vapor pressure of water is at least two orders of magnitude greater than octanoic acid.

Non-aqueous chlorine dioxide solutions may be compatible with both non-aqueous and aqueous environments. Addition of hydrotropes can facilitate the use of non-aqueous chlorine dioxide solutions in aqueous environments. When a water insoluble non-aqueous carboxylic acid is used to generate non-aqueous chlorine dioxide, the resultant non-aqueous chlorine dioxide may be used to generate an aqueous chlorine dioxide solution by mixing with water and then extracting the non-soluble carboxylic salt from the aqueous chlorine dioxide. The non-aqueous carboxylic acid may then be recovered from a water-based system (e.g., via extraction), re-protonated (e.g., via ion exchange) and re-used to generate additional non-aqueous chlorine dioxide.

Applications

The non-aqueous chlorine dioxide solutions may be used as a disinfectant, sterilizing agent and/or bleaching agent in a number of industries including, but not limited to, the dairy industry, the food and beverage industry, the pulp and paper industries, water and wastewater treatment industries, the fruit and vegetable processing industries, various canning plants, the poultry industry, the beef processing industry and other miscellaneous food processing applications. The non-aqueous solutions may be used in aqueous-based systems (e.g., cooling water, drinking water, flume waters, water used in the processing of meat, poultry, fruits, vegetables, and beverages, and water used in the manufacture of paper products). Additionally, the non-aqueous solutions may be used in oil-based or oil-in-water-based systems (e.g., cutting oils, petroleum-based products, lubricants and confectionary products).

Methods of disinfecting or sanitizing an object are provided. An object may be disinfected by applying the non-aqueous chlorine dioxide solution to the object. The non-aqueous chlorine dioxide solution may be applied by any method known to those of skill in the art, including but not limited to, brushing, spraying, sponging, scrubbing, dipping, soaking, submerging, or coating the object. Application of the non-aqueous chlorine dioxide solution to the object may result in a decrease in the microbial load on the object. For example, the number of viable bacteria (or bacterial load) found on an object after treatment with the non-aqueous chlorine dioxide solution may be reduced by at least about 50% relative to the pretreatment bacterial load, suitably the bacterial load is reduced by at least about 75%, at least about 80%, at least about 85%, at least about 90%, at least about 95%, at least about 98%, or at least about 99%.

The methods may be used to disinfect or sanitize a wide variety of objects that will be apparent to those of skill in the art. The types of objects that may be disinfected include, but are not limited to, food products, containers, plants, surfaces, mechanical devices, animals, animal carcasses, and animal habitats. Food products that may be treated with a non-aqueous chlorine dioxide solution include, but are not limited to, fruits, vegetables, meat products, poultry products, seafood products, dairy products, beverages, ready-to-eat foods, confectionary products and raw foods. Many types of surfaces may be disinfected using the methods provided herein, including but not limited to, tables, floors, countertops, walls, hand rails, guard rails, toilets, showers, and baths. Animals and animal carcasses include but are not limited to, domestic animals, livestock, poultry, and fish.

In one embodiment, the non-aqueous chlorine dioxide solution may be used to disinfect the carcasses of slaughtered animals by applying (e.g., spraying) the non-aqueous chlorine dioxide solution on the carcass. The addition of a hydrotrope, such as sodium cumene sulfonate, to the non-aqueous chlorine dioxide solution may improve the wetting nature of the mixture. The non-aqueous chlorine dioxide solution may also be applied to animal carcasses to minimize or prevent dehydration during the freezing process. The current freezing practice of air chilling dehydrates the animal carcasses and ultimately affects the texture and color of the meat. The non-aqueous chlorine dioxide solution may be applied to the carcass by, for example, brushing, dipping or spraying.

In other embodiments, the non-aqueous chlorine dioxide solution may be used as a surface sanitizer. The non-aqueous chlorine dioxide solutions can provide superior antimicrobial action, penetrate and remove biofilms, treat mold and mildew and control odor. The non-aqueous solution may be applied to the surface by, for example, brush, sponge or spray bottle. Alternatively, the surface could be dipped, soaked or bathed in the non-aqueous chlorine dioxide solution.

In other embodiments, the non-aqueous chlorine dioxide solution may be used to wash fruits (e.g., apples, oranges and grapefruits) and vegetables (e.g., potatoes and lettuce). Chlorine dioxide has the ability to kill spores, viruses and fungi at relatively low concentrations. The non-aqueous solution may be applied to the fruit and/or vegetables by, for example, brushing, dipping or spraying.

Methods of disinfecting or sanitizing a liquid are also provided. A liquid may be disinfected by adding the non-aqueous chlorine dioxide solution to the liquid. The addition of the non-aqueous chlorine dioxide solution to the liquid is capable of reducing the bacterial load of the liquid as compared to an untreated sample. Addition of the non-aqueous chlorine dioxide solution to the liquid may result in a decrease in the microbial load in the treated liquid. For example, the bacterial load found in the liquid after treatment with the non-aqueous chlorine dioxide solution may be reduced by at least about 50% relative to the bacterial load prior to treatment, suitably the bacterial load is reduced by at least about 75%, at least about 80%, at least about 85%, at least about 90%, at least about 95%, at least about 98%, or at least about 99%.

Those of skill in the art will immediately envision liquids that may be disinfected with non-aqueous chlorine dioxide. Such liquids include, but are not limited to, drinking water, cooling water, flume water, water used in food processing, water used in the manufacture of paper products, wastewater, a lubricant, an oil-based cleanser, or a water-based cleanser. The non-aqueous chlorine dioxide solution may be added to the liquid in an amount effective to reduce the bacterial load of the liquid. The final concentration of chlorine dioxide in the disinfected liquid may be at least about 0.5 parts per million (ppm), suitably at least about 1 ppm, suitably at least about 5 ppm, more suitably at least about 10 ppm. The amount of chlorine dioxide can be quantified using method number 8138 from the Hach Chemical Company with a DR/4000 spectrophotometer.

In yet another embodiment, the non-aqueous chlorine dioxide solution can be added to conveyor lubricants, such as a silicone-based or Teflon-based conveyor lubricant, to control the growth of microorganisms on conveyor systems. Methods of reducing bacterial growth on conveyor systems are provided. The methods include adding the non-aqueous chlorine dioxide solution to a conveyor lubricant, and applying the conveyor lubricant to a conveyor system. The conveyor lubricants include silicone-based and Teflon-based conveyor lubricants.

Before any examples of the invention are provided, it is to be understood that the invention is not limited in its application to the details of construction and the arrangement of components set forth in the following examples. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof are meant to encompass the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

EXAMPLES

Example 1

A non-aqueous solution of chlorine dioxide was prepared by mixing 0.1143 g sodium chlorite (CAS #7758-19-2) with 100 mL octanoic acid (CAS #124-07-2). The solution turned progressively yellow over time, indicating the formation of $ClO_2$. No precipitate was noted and the solution remained yellow for at least twelve months when stored in a glass container with a Teflon closure in the dark at room temperature (about 68-72° F.).

Thus, the invention provides, among other things, a method for producing a non-aqueous chlorine dioxide solution and methods for using the same. Various features and advantages of the invention are set forth in the following claims.

What is claimed is:

1. A method of making a non-aqueous chlorine dioxide solution comprising: combining a solid chlorite salt and a liquid non-aqueous carboxylic acid to produce a non-aqueous chlorine dioxide solution.

2. The method of claim 1, wherein the chlorite salt is sodium chlorite.

3. The method of claim 1, wherein the non-aqueous carboxylic acid is a fatty acid of the formula RCOOH, wherein R is an aliphatic group.

4. The method of claim 3, wherein the non-aqueous carboxylic acid is octanoic acid.

5. The method of claim 1, wherein the concentration of chlorite salt is at least about 0.1 g per liter non-aqueous carboxylic acid.

6. The method of claim 1, wherein the concentration of chlorite salt is at least about 1 g per liter non-aqueous carboxylic acid.

7. The method of claim 1, further comprising adding a hydrotrope to at least one of the non-aqueous carboxylic acid and the non-aqueous chlorine dioxide solution to produce a water-compatible non-aqueous chlorine dioxide solution.

8. The method of claim 1, further comprising adding an antimicrobial to at least one of the non-aqueous carboxylic acid and the non-aqueous chlorine dioxide solution.

9. The method of claim 1, further comprising adding a wetting agent to at least one of the non-aqueous carboxylic acid and the non-aqueous chlorine dioxide solution.

* * * * *

UNITED STATES PATENT AND TRADEMARK OFFICE
CERTIFICATE OF CORRECTION

PATENT NO.       : 8,563,019 B2
APPLICATION NO.  : 12/933295
DATED            : October 22, 2013
INVENTOR(S)      : Michael F. Coughlin Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 77 days.

Signed and Sealed this
Fifteenth Day of September, 2015

Michelle K. Lee
*Director of the United States Patent and Trademark Office*